(12) United States Patent
Kellan

(10) Patent No.: US 6,261,321 B1
(45) Date of Patent: *Jul. 17, 2001

(54) PHAKIC OR APHAKIC INTRAOCULAR LENS ASSEMBLY

(76) Inventor: Robert E. Kellan, 49 Sutton Hill Rd., N., Andover, MA (US) 01845

( * ) Notice: Subject to any disclaimer, the term of this patent is extended or adjusted under 35 U.S.C. 154(b) by 0 days.

This patent is subject to a terminal disclaimer.

(21) Appl. No.: 09/727,141

(22) Filed: Nov. 30, 2000

Related U.S. Application Data

(63) Continuation-in-part of application No. 09/652,505, filed on Aug. 31, 2000.
(60) Provisional application No. 60/154,508, filed on Sep. 17, 1999, provisional application No. 60/152,690, filed on Sep. 7, 1999, and provisional application No. 60/151,991, filed on Sep. 1, 1999.

(51) Int. Cl.$^7$ ........................................................ A61F 2/16
(52) U.S. Cl. ........................................ 623/6.51; 623/6.43
(58) Field of Search ................................. 623/6.11, 6.38, 623/6.4, 6.43, 6.51, 6.52, 6.54

(56) References Cited

U.S. PATENT DOCUMENTS

| | | | |
|---|---|---|---|
| 4,053,953 | 10/1977 | Flom et al. | 3/13 |
| 4,254,509 | 3/1981 | Tennant | 3/13 |
| 4,285,072 | 8/1981 | Morcher et al. | 3/13 |
| 4,676,792 | 6/1987 | Praeger | 623/6 |
| 4,710,195 | 12/1987 | Giovinazzo | 623/6 |
| 4,711,638 | 12/1987 | Lindstrom | 623/6 |
| 4,816,032 | 3/1989 | Hetland | 623/6 |
| 4,994,080 | 2/1991 | Shepard | 623/5 |
| 5,133,747 | 7/1992 | Feaster | 623/6 |
| 5,928,282 | 7/1999 | Nigam | 623/6 |
| 6,015,435 | 1/2000 | Valunin et al. | 623/6 |
| 6,083,261 | 7/2000 | Callahan et al. | 623/6.38 |
| 6,110,202 | 8/2000 | Barraquer et al. | 623/6.43 |
| 6,142,999 | 11/2000 | Brady et al. | 606/106 |

*Primary Examiner*—Dinh X. Nguyen
(74) *Attorney, Agent, or Firm*—McDermott, Will & Emery

(57) ABSTRACT

An intraocular lens assembly for use in the phakic or aphakic eye is provided. In the preferred embodiment, the intraocular lens assembly is suitable for the correction of myopia, hyperopia, astigmatism.

The lens assembly has a lens having a circumferential edge, and a first haptic and a second haptic, which extend from the edge of the lens. Each of the haptics has a first leg extending from the lens edge to a distal end, and a second leg extending from the lens edge to distal end, and a transverse member extending between the distal ends of each first and second leg. The transverse member can be substantially straight or bowed inward toward the lens. Each leg has a footplate at its distal end.

Each leg of each haptic may be in inwardly bowing, straight, and outwardly bowing. Additionally, each leg may have the same or different shape from the other legs. In a one embodiment, the first and second legs of the first and second haptics are outwardly bowing. In another embodiment, the first and second legs of the first and second haptics are inwardly bowing.

The intraocular lens assembly is made from a flexible material. Preferably the material is hydrogel, collagen, collamar, collagel, acrylate polymers, polymethylmethacrylate polymers, silicone polymers, and composites thereof.

In one embodiment, the intraocular lens assembly is foldable. In another embodiment, the intraocular lens assembly is firm.

17 Claims, 7 Drawing Sheets

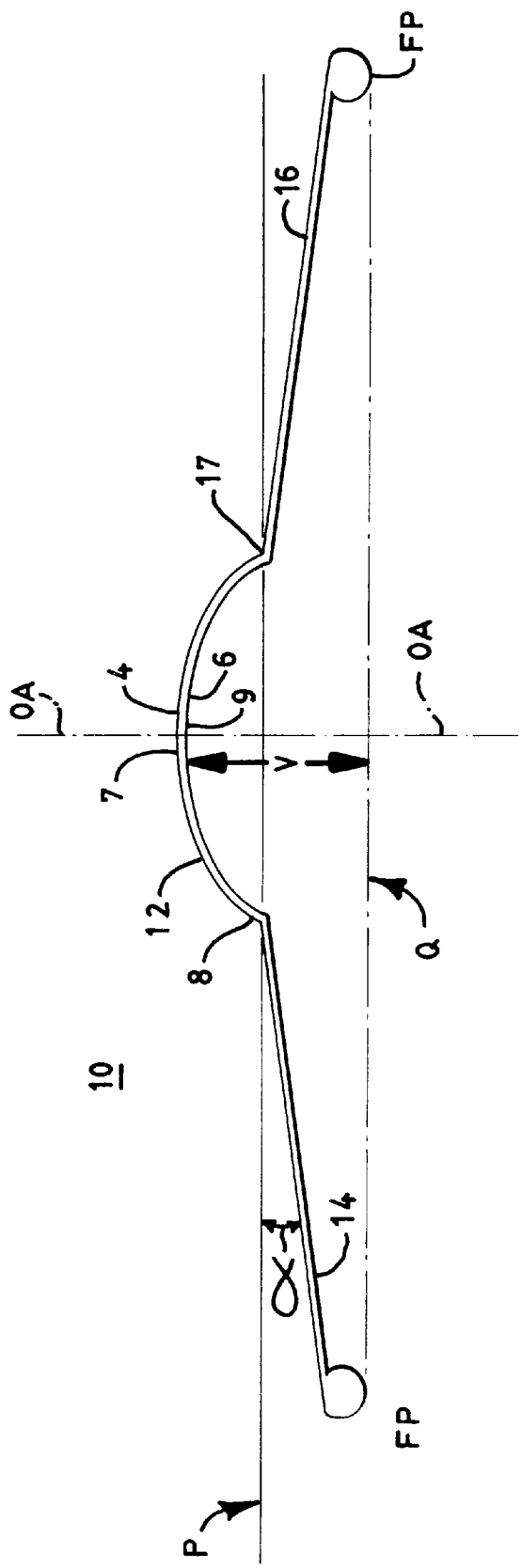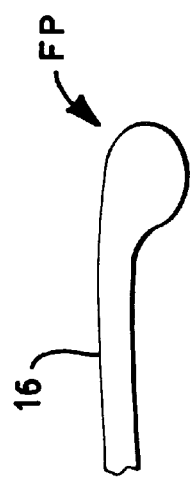
FIG. 2
FIG. 3

PHAKIC OR APHAKIC INTRAOCULAR LENS ASSEMBLY

CLAIM OF PRIORITY

This application is a continuation-in-part of U.S. patent application Ser. No. 09/652,505, filed Aug. 31, 2000, which claims priority to U.S. provisional patent applications No. 60/151,991, filed Sept. 1, 1999; 60/152,690, filed Sept. 7, 1999; and Ser. No. 60/154,508, filed Sept. 17, 1999.

FIELD OF THE INVENTION

The present invention relates to implantable intraocular lenses suitable for the correction of myopia, hyperopia, and astigmatism.

BACKGROUND OF THE INVENTION

Implantation of artificial lenses into the human eye has been a standard technique for many years, both to replace the natural crystalline lens (aphakic eye) and to supplement and correct refractive errors of the natural lens (phakic eye).

Various diseases and pathological conditions can result in damage to the natural crystalline lens, such as opacification that occurs as a result of cataracts. Intraocular artificial lens implantation into the anterior chamber or posterior chamber of the eye is a known technique for treating cataracts.

Intraocular corrective lenses have been developed for the treatment of various vision problems of the eye, such as myopia, hyperopia and astigmatism in the phakic eye. However, the use of currently available phakic intraocular lenses has been less than satisfactory in the long-term correction of refractive errors because the overall design of these lenses can result in damage to the natural crystalline lens.

The ideal phakic intraocular lens must be implantable through a self-scaling, clear corneal incision. It must be made of a very biocompatible material. It must have minimal touch with the uveal structures of the eye, no contact with the natural crystalline lens, and no compromise of the angle of the eye.

Currently, most phakic lenses are iris-fixated lenses, angle-fixated lenses, or sulcus-fixated, posterior chamber lenses.

Iris-fixated lenses require a 5.5 to 6 mm incision and involve a difficult insertion surgical technique. Angle-fixated lenses generally a 5.5 mm incision. These lenses also require very accurate white-to-white measurements, which are difficult to obtain. Angle-fixated lenses can also cause pupillary distortion. Sulcus-fixated/posterior chamber lenses are less difficult surgically to insert than iris-fixated lenses, but are more difficult to inset than angle-fixated lenses. There have been reports of cataract formation after insertion of these lenses.

Examples of implantable intraocular lenses include various design configurations. Generally, the lenses are attached in some manner within the eye, usually by sutures to the iris, or some other supporting means, such as arms, or haptics, extending from the optical lens portion of the intraocular lens.

U.S. Pat. No. 4,053,953 describes an artificial intraocular lens for the aphakic eye. The lens is secured in the posterior chamber by a system of posts that protrude through the iris attached to retaining rings.

U.S. Pat. No. 6,015,435 describes a self-centering phakic intraocular lens inserted in to the posterior chamber lens for the correction of myopia, hyperopia, astigmatism, and presbyopia. Haptic bodies are attached to optical body and extend outward from tangent points at the edge of lens in at least two generally opposite directions. Protruding surfaces protrude into pupil such that the iris interferes slightly with lens movement and provides the centering force to keep lens in place.

U.S. Pat. No. 4,710,195 describes a posterior chamber lens, particularly adapted for patients with glaucoma and cataracts. Two haptics are connected to optic body at its edge. The haptics are offset from the other by 180 degrees and extend circumferentially around the edge of the optic portion. The haptics end in enlarged "blocking segments".

U.S. Pat. No. 4,676,792 describes an artificial intraocular lens device implantable in the anterior chamber of the eye (in front of the iris) for treating myopia. The optic body has three or four "J" shaped haptics that terminate with solid footplates to anchor the lens. In one embodiment, haptics are positioned circumferentially around the edge of optic body approximately 90 degrees apart. The haptics are grouped in pairs so that each pair is oriented such that the respective curved surfaces of solid footplates face each other.

U.S. Pat. No. 5,133,747 describes an intraocular lens device that is partially or completely within the anterior capsular surface of the human crystalline lens. In one embodiment, the optic body has asymmetrical haptics extending outwardly from opposite sides of the periphery of the optic body. In one embodiment, "J" shaped haptics extend from the periphery of the optic body in a manner that encircles optic body. In another configuration, the haptics extend tangentially away from body, then reverse direction, giving the device an overall "S" shape with the lens at center portion of the S. The device is secured in place with an adhesive.

U.S. Pat. No. 5,928,282 describes a refractive intraocular lens for implantation into the anterior chamber. The lens body has elongated, ovoid-disc shaped haptics extending from its peripheral edge.

U.S. Pat. No. 4,994,080 describes optical lens devices having an optical body with multiple perforations and two J shaped haptics that terminate in footplates.

U.S. Pat. No. 6,083,261 describes an intraocular lens having crossed haptics for implantation into either phakic or aphakic eye.

U.S. Pat. No. 4,285,072 describes closed loop haptics on an intraocular lens. When positioned in the eye, the circular arched haptics without footplates extend rearward from the optic body, then angle sideways to allow the arch to rest in the angle to keep the lens in place. This design proved to be physiologically unsuitable for use.

There is a need for an intraocular lens device that overcomes the problems of the existing intraocular lenses and yet provides ophthalmic surgeons with an intraocular lens that addresses the refractive errors in patients' eyes safely and reversibly.

SUMMARY OF THE INVENTION

An intraocular lens (IOL) assembly and method for correcting myopia, hyperopia and astigmatism using the intraocular lens assembly are provided. The lens assembly has a lens having a circumferential edge, and a first haptic and a second haptic, which extend from the edge of the lens. Each of the haptics has a first leg extending from the lens edge to a distal end, and a second leg extending from the lens edge to distal end, and a transverse member extending between the distal ends of each first and second leg. The transverse member can be substantially straight or bowed inward toward the lens. Each leg has a footplate at its distal end. Each leg of each haptic may be in inwardly bowing, straight, and outwardly bowing. Additionally, each leg may have the same or different shape from the other legs.

In a one embodiment, the first and second legs of the first and second haptics are outwardly bowing. In another embodiment, the first and second legs of the first and second haptics are inwardly bowing.

The intraocular lens assembly is made from a flexible material. Preferably the material is hydrogel, collagen, collamar, collagel, acrylate polymers, methacrylate polymers, silicone polymers, and composites thereof. In one embodiment, the intraocular lens assembly is foldable. In another embodiment, the intraocular lens assembly is firm.

The invention thus provides an intraocular artificial lens assembly that is made of existing biocompatible, flexible foldable materials. Because it is foldable, the intraocular lens assembly of the invention can be inserted through a small, self-sealing, clear corneal incision. Moreover, the intraocular lens assembly is explantable through an incision the size of the original insertion incision. Further, the intraocular lens assembly has minimal contact with the anatomic structures of the eye.

The intraocular lens assembly of the invention can be usefully implanted into the eye as either a refractive phakic intraocular lens or an aphakic intraocular lens, depending on the location in the eye into which the intraocular lens is implanted. For example, the intraocular lens assembly of the invention can, following the appropriate implantation, be either an angle-supported phakic intraocular lens located in front of the iris or a sulcus-supported phakic intraocular lens located behind the iris. Moreover, because of the haptic design, the intraocular lens assembly of the invention can, when placed in the capsular bag of the eye, provide accommodation for the patient. Advantageously, post-operative atropinization of the optic ciliary muscle is not required for the intraocular lens assembly of the invention (when implanted either as a refractive phakic intraocular lens or an aphakic intraocular lens) to achieve accommodation.

BRIEF DESCRIPTION OF THE DRAWINGS

The invention, and the various features thereof, may be more fully understood from the following description, when read together with the accompanying drawings, in which:

FIG. 2 shows a cross sectional view of the lens assembly of FIG. 1 along axis A.

FIG. 3 shows a sectional view of one of the footplates of the lens assembly of FIG. 1.

DETAILED DESCRIPTION OF THE INVENTION

In the eye, the natural lens of the eye separates the aqueous humor from the vitreous body. The iris separates the region between the cornea or anterior of the eye and the lens into an anterior chamber and a posterior chamber. The natural crystalline lens is contained in a membrane known as the capsule or capsular sac. When the natural lens is removed from the eye, the capsule may also be removed (intracapsular excision), or the anterior portion of the capsule may be removed with the natural crystalline lens, leaving the posterior portion of the capsule intact (extracapsular extraction), often leaving small folds or flaps from the anterior portion of the capsule. In an intraocular implant, the artificial lens may be inserted in the anterior chamber, the posterior chamber, or the capsular sac.

The design of intraocular lens assembly of the present invention overcomes the problems with the prior intraocular devices. The intraocular lens assembly of the invention is primarily designed for placement in the anterior chamber of the eye and use as a refractive lens for the phakic eye. However, the unique design of the intraocular lens assembly also permits its use in the aphakic eye, and placement in the posterior chamber sulcus and the posterior chamber bag. The intraocular lens assembly described herein is suitable for correction of myopia, hyperopia, and astigmatism without compromising the anatomy or physiology of the eye.

The intraocular lens assembly of the invention is made from a biocompatible, flexible, material. In a preferred embodiment, the material is also a foldable material, which allows insertion of the device through small incisions, usually 3 mm or less. Since the device is preferably inserted into the anterior chamber of the eye, there is no contact with the natural crystalline lens, so that cataract formation is minimized. The design provides minimal contact with other tissues in the eye. Furthermore, the device can be easily removed and reinserted as needed. The combination of flexible materials and the haptic design allows the device to withstand some deforming forces, such as the patient rubbing his eyes, without the device breaking, warping, or becoming disengaged from the eye.

Figure 1:
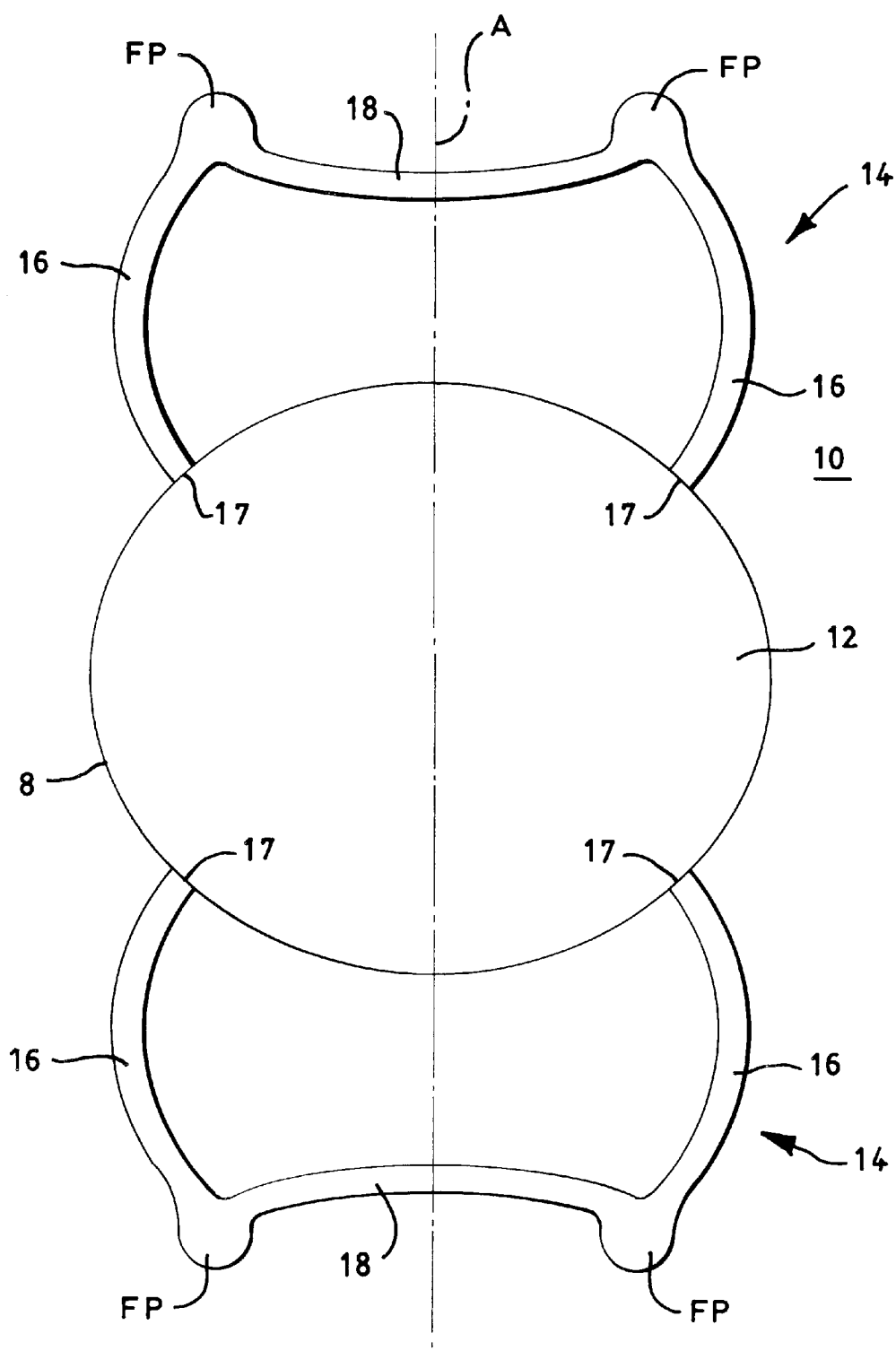
FIG. 1 shows a top view of the lens assembly of the invention.

As shown in FIG. 1, the intraocular lens assembly 10 includes a lens portion (the "optic") 12 and two sets of haptics 14 extending from periphery 8 of optic 12. Each set of haptics 14 has pair of legs 16 that connect at their proximal ends to periphery 8 at points 17, and extend toward footplates FP at their distal ends. Legs 16 are connected together in pairs substantially near their distal ends by transverse member 18. In the embodiment shown in FIG. 1, legs 16 are outwardly bowing; each pair is joined by an inwardly bowing transverse member 18. Preferably, proximal ends of legs 16 are spaced equidistant around periphery 8 of optic 12. This symmetry provides the most comfort to the patient and stability of the lens. Alternatively, legs 16 may be attached at differently spaced, non-equidistant points on periphery 8 as needed, depending upon the individual eye anatomy or vision requirements.

FIG. 2 shows a cross section of the embodiment of FIG. 1 along axis A. Optic 12 constitutes the optical portion of the lens assembly. The optic 12 comprises an outer surface 4 and inner surface 6. The combination of inner surface 4 and outer surface 6 may result in the optical portion being substantially planar, convex, plano-convex and concave, bi-convex, concave-convex, or any combination thereof. Preferably, the shape is substantially concave-convex. The diameter of optic 12 can vary as needed to accommodate the angle-to-angle measurement of the eye and curvature of the eye. The overall length of the intraocular lens (optic and haptics) to be inserted into an individual patient's eye is determined by adding a 1 mm white-to-white measurement of the patient's eye. Optic 12 preferably has a 6 mm optical zone.

Optic 12 may be ground to the required diopter measurements necessary for vision correction. The lens may be a negative or positive meniscus lens and may include correction for astigmatism. Depending on the refractive index of the material used, and the required vision correction, optic 12 may have the same thickness at central portion 7 and periphery 8, or central portion 7 may be thinner than periphery 8. Preferably the thickness of optic 12 is 1 mm.

As shown in FIG. 2, haptics 14 extend from periphery 8 of optic 12 at a slight angle from a horizontal (as shown) axis P perpendicular optical axis OA. Depending upon the curvature and size of the optic lens needed, haptics 14 may be offset from horizontal axis P by angle α Vault distance V is the height of the lens assembly measured from a line Q, which is drawn horizontally (as shown) between footplates FP, to the apex 9 of inner surface 6 and parallel to optical axis OA. Angle α may be 2 or 3° or more as needed, provided that angle α is one that, when in combination with the size and shape of the optical element and the anatomical angle of the eye, provides a 1 mm vaulting distance V. The vaulting distance insures adequate clearance for the intraocular lens assembly to be situated between the natural crystalline lens and the cornea in the anterior chamber.

The footplates FP of the haptics are integrally formed on the distal end of each leg 16, preferably near or at the point where leg 16 connects to the transverse member 18. Footplates FP are preferably lenticular-shaped (shown in FIG. 3) to allow for minimal contact with the eye structures yet provide the required stability for the desired visual results.

Figure 4:
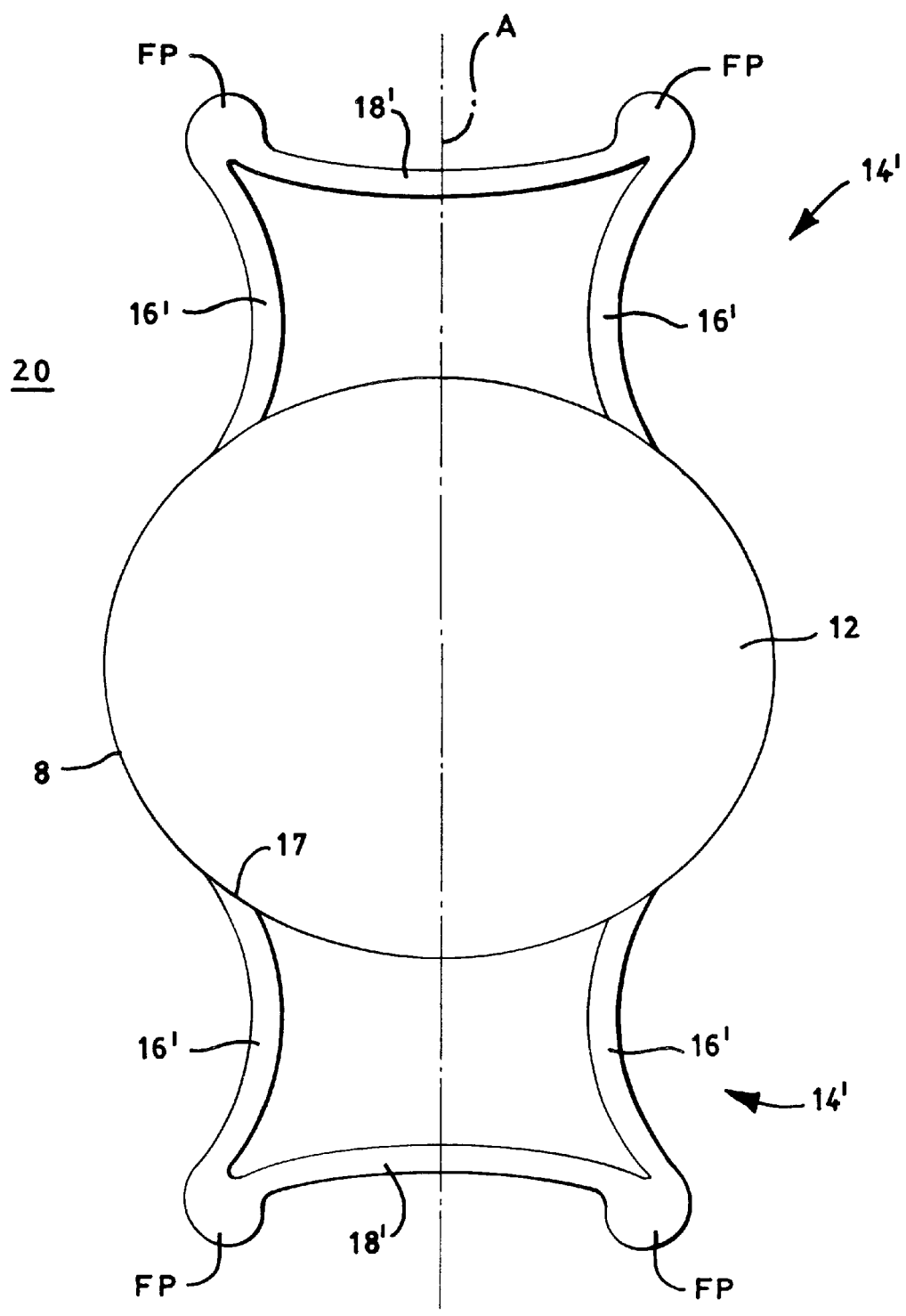
FIG. 4 shows a top view of an alternative lens assembly of the invention.
Figure 5A:
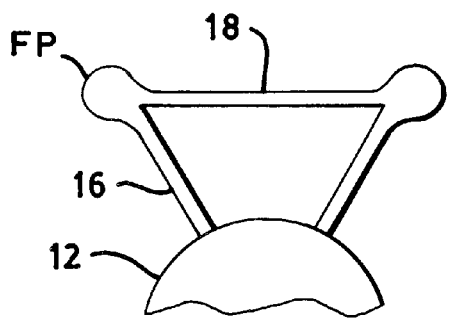
FIG. 5 shows alternate embodiments of the lens assembly.
Figure 5D:
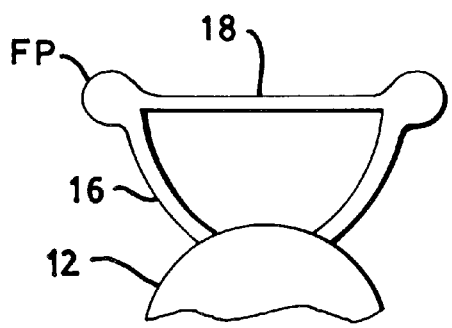
Figure 5B:
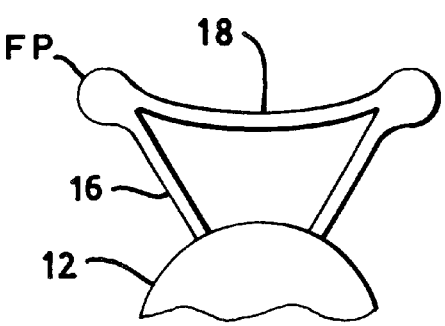
Figure 5E:
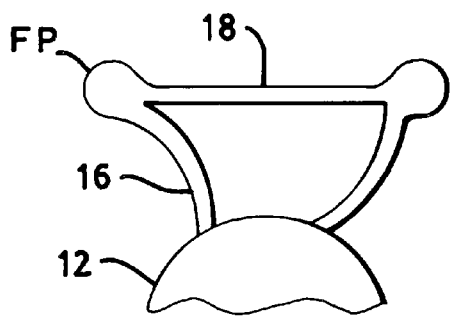
Figure 5C:
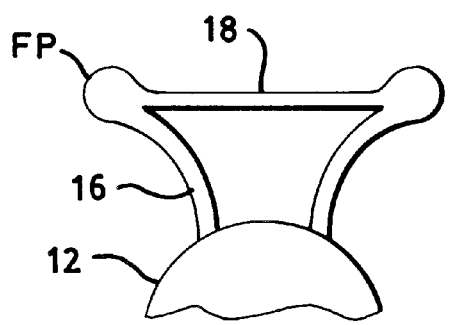
Figure 5F:
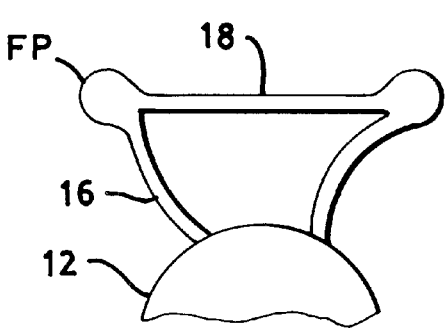
Figure 5G:
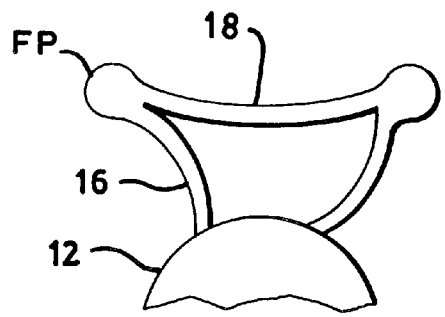
Figure 5H:
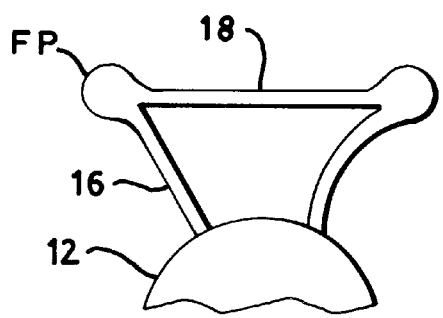
Figure 5J:
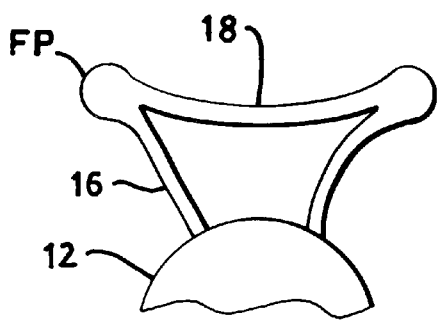
Figure 5I:
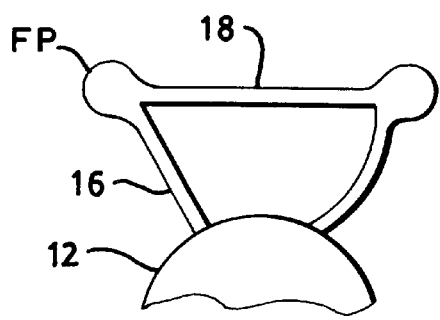
Figure 5K:
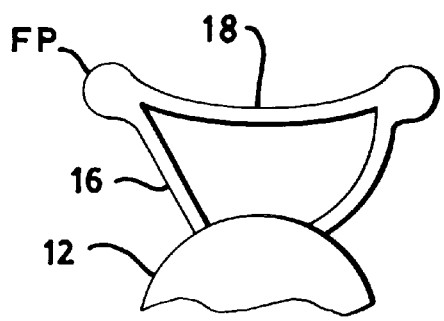

An alternate embodiment of the invention is shown in FIG. 4. In that figure, lens assembly 20 includes an optic 12 and haptics 14'. Lens assembly 20 is generally similar to the assembly 10 of FIGS. 1 and 2, but has haptics 14' with inwardly bowing legs 16' in contrast to the assembly 10 that has haptics 14 with outwardly bowing legs 16. As with lens assembly 10, the lens assembly 20 is an anterior chamber angle supported intraocular lens preferably constructed of a biocompatible, foldable material such as hydrogel to allow for insertion through a clear corneal incision.

Other non-limiting configurations of haptics are shown in FIGS. 5A–K. In these embodiments, one or both of legs 16 of each haptic can be straight, inwardly bowing, outwardly bowing, or combinations thereof. Each haptic may have the same or different leg configurations as the other haptic.

In all embodiments, the transverse member 18 may be substantially straight or inwardly bowing. "Substantially straight" includes either straight or slight, outward-bowing deviations from straight, provided that the outward bow of the transverse member 18 does not extend beyond the footplates FP in the direction of axis A in a manner that interferes with the footplates resting in the angle of the eye (see, FIG. 1).

The preferred embodiment intraocular lens assembly of the invention is designed to be foldable to facilitate insertion through small incisions, generally 3 mm in length or less. The device can be folded along axis A (shown in FIG. 1), transverse to axis A, at an angle offset from axis A, or in multiple directions. The device can be folded in the optic body, at any point in the haptics, at the junction points between the optic body and the haptics, or all of the above. The device can be folded with single or multiple folds along each direction.

Suitable materials for the lens assembly of the invention are solid, flexible, foldable optical, non-biodegradable materials such as hydrogel, collamer, collagel (hydrogel-collagen blends) acrylic polymers, polymethylmethacrylate (PMMA) and silicone polymers. The lens assembly may also be made of a composite of materials, i.e. where the haptics are fabricated from one material and the optics from another material, for example, acrylic optics and hydrogel haptics. Where the lens assembly is used in the aphakic eye, flexible, but less foldable, materials may be preferred. For example, for the aphakic eye, the lens assembly may be made of all PMMA or a composite of PMMA optics and prolene haptics.

By way of example, the lens assembly may be made as a sterile UV-absorbing acrylic foldable form, for example using the same material as the AcrySof™ IOL manufactured by Alcon Laboratories, Inc. Moreover, in various forms the lens may be used in the anterior chamber, the posterior chamber sulcus and the posterior chamber bag.

FIG. 5 shows the intraocular lens device 10 of the invention implanted in the anterior chamber 32 of the eye 30 and fixated in the angle 31. Lens assembly 10 is positioned in anterior chamber 32, between cornea 34 and iris 36, with optic body 12 positioned over pupil 38 and haptics 14, with footplates FP extending into angle 31. Movement of natural crystalline lens 42 is unobstructed in the posterior chamber 40 by device 10. The low vault height insures that device 10 does not contact cornea 34.

With this configuration, the footplates of intraocular lens rests in angle 31, which steady the intraocular lens in the proper position.

As mentioned above, the intraocular lens assembly of the invention can be usefully implanted into the eye as either a refractive phakic intraocular lens assembly or an aphakic intraocular lens assembly. Phakic intraocular lens implantation is becoming more popular because of their good refractive and visual results and because they are relatively easy to implant in most cases (Zaldivar & Rocha, 36 Int. Ophthalmol. Clin. 107–111 (1996); Neuhann et al., 14 J. Refract. Surg. 272–279 (1998); Rosen & Gore, 24 J. Cataract Refract. Surg. 596–606 (1998); Sanders et al., 24 J. Cataract Refract. Surg. 607–611 (1998). The implantation can be performed by an ordinarily skilled ophthalmologist. Little surgical injury occurs to the ocular tissues during such implantation. When the surgical quality is not compromised, the results are highly predictable, immediate, and lasting.

Phakic lens assembly implantation using the intraocular lens assembly of the invention has advantages over other forms of surgical vision enhancement. Unlike laser surgery, the implants are removable. The natural crystalline lens remains, and the patient doesn't lose the ability to accommodate. Refractive surgery by phakic intraocular lenses among patients with hyperopia is not yet as popular as patients with myopia, but primarily because such surgery has not been available for as long (Fechner et al., 24(1) J. Cataract Refract. Surg. 48–56 (1998)).

Figure 6:
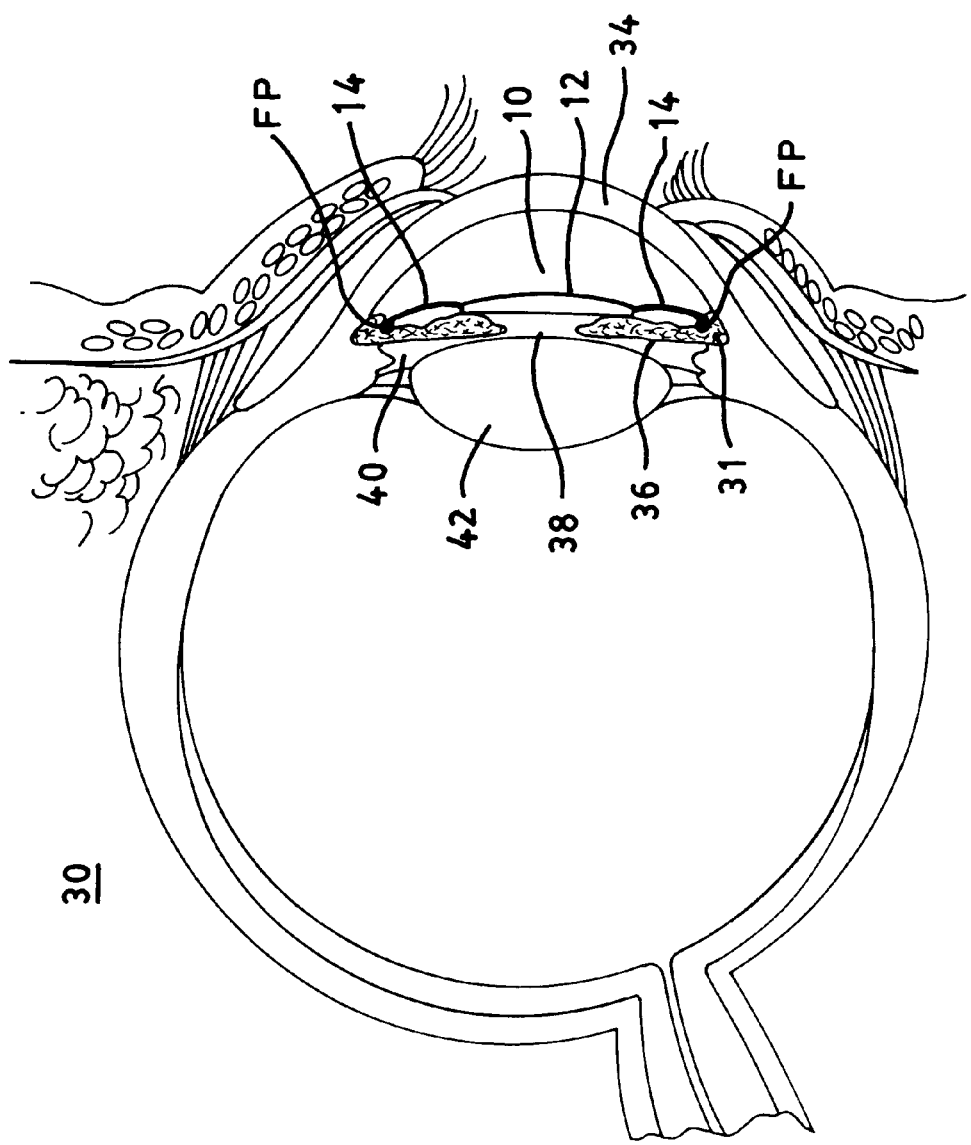
FIG. 6 shows a sectional view of an eye with the lens assembly of the invention deployed.
Figure 7:
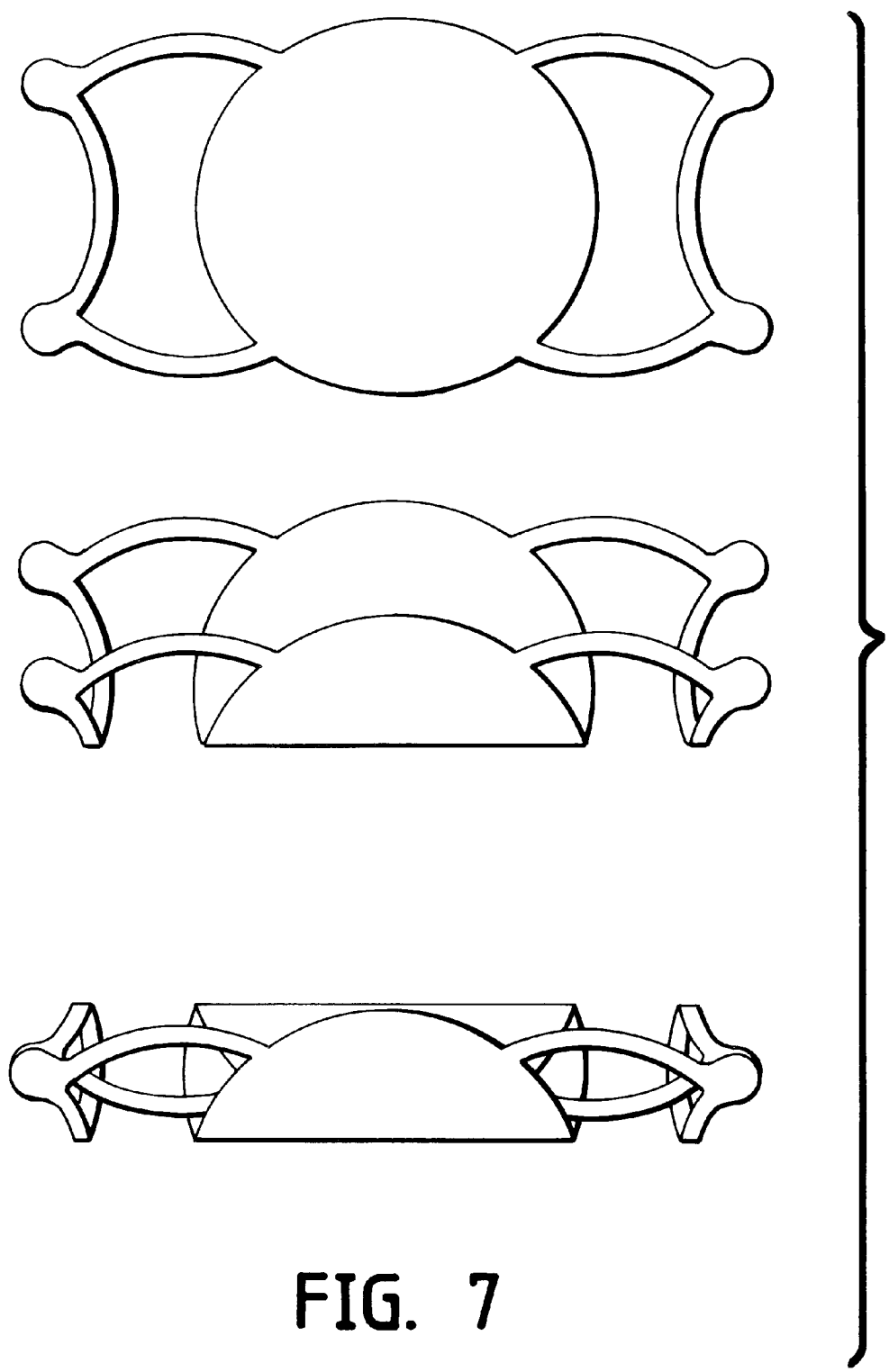
FIG. 7 shows a diagram of the folding sequence of the lens assembly of the invention.

For a phakic lens assembly implantation, the intraocular lens assembly of the invention is preferably located in the anterior chamber of the eye. Following the appropriate implantation, the intraocular lens of the assembly invention can be either an angle-supported phakic intraocular lens located in front of the iris (see, FIG. 6) or a sulcus-supported phakic intraocular lens located behind the iris (contrast with the lens assemblies described in the BACKGROUND OF THE INVENTION). The haptic lens features of the intraocular lens assembly of the invention fixate the distal haptic portions of the lens, thus preventing dislocation and slipping or shifting of the intraocular lens from its proper position.

The implantation assembly of the intraocular lens assembly of the invention can generally be performed as provided by (Singh, emedicine Ophthalmology (2000) http://www.emedicine.com/cgi-bin/foxweb.exe/showsection@d:/em/ ga?book=oph&topicid=662):

First, the administration of local antibiotic drops is begun. A useful antibiotic is Tobramycin 0.3%, 1 drop, 6 times a day. Then, the pupil of the eye is contracted with 1% pilocarpine drops, administered for example at 15-minute intervals, starting 45 minutes before surgery. Drops (such as NSAID drops) are administered 2 times before surgery to minimize inflammation.

General anesthesia can be performed on the patient, but local anesthesia is preferred. For local anesthesia, 2% lidocaine with 7.5 U/ml hyaluronidase can be given 10 minutes before surgery. Orbital compression is applied to make the eye soft and to reduce orbital pressure.

For preparation of the surgical field, the periorbital skin of the patient is painted with iodine, then 5% povidine is applied. 5% povidine is also applied two-three times to the lid margin and the conjunctival fornices. Then, the eye is washed with saline.

An eye speculum is used for exposure of the surgical field. Upper and lower lid sutures, as well as superior rectus sutures can be applied in place of the speculum. (A sutureless procedure can also be used.) Adhesive plastic, applied to the surface of the eyelids, is used to pull the eyelashes.

For making small intraoperative incisions, an side port (for example, 0.6 mm) is made in the anterior chamber. This injection is started at the opposite limbus. As the aqueous fluid drains, it is replaced, for example, with a viscoelastic agent. The depth of the anterior chamber is not reduced at any time.

In one embodiment, for implantation of the intraocular lens assembly of the invention into the eye, two side ports are made to introduce the instruments that are used to fix the iris to the haptics. The width of the incision depends on the diameter of the intraocular lens assembly of the invention (being, for example, 4–5 mm). The incision may be made at the limbus or in the clear cornea. If a pocket section is made, wound closure (see, below) can be made without sutures. The intraocular lens assembly of the invention can then be introduced in the pre-crystalline space with angled-suture forceps the lens is positioned, for example, behind the iris on a horizontal axis with a cyclodialysis spatula. The intraocular lens assembly of the invention is then manipulated to center the optic on the pupil. During implantation of the phakic intraocular lens assembly of the invention into the anterior chamber, the lens is centered and fixed so that it does not slip out of position. The lens can be positioned between the cornea and the iris, but avoiding contact with either to prevent corneal damage, proliferation of corneal epithelium on the anterior surface of the lens causing opacification, or iris. If the lens is not positioned properly with respect to the pupil, too much light may be admitted to the retina, causing serious vision difficulties. The haptics generally lodge in the angle of the anterior chamber. Also, the anterior chamber of the eye is filled with the aqueous humor, a fluid secreted by the ciliary process, passing from the posterior chamber to the anterior chamber through the pupil, and from the angle of the anterior chamber it passes into the spaces of Fontana to the pectinate villi through which it is filtered into the venous canal of Schlemm. The implanted lens is positioned so the flow of fluid is not blocked.

After the intraocular lens assembly of the invention is implanted, the viscoelastic material (if previously introduced into the eye chambers) is removed from the anterior and posterior chambers of the eye with an aspiration syringe (such as a 24-gauge cannula). The intraocular lens assembly of the invention is fixed to the anterior surface of the iris by the haptics of the lens. To achieve fixation, the haptic holds a fold of the iris on either side of the pupil. The anterior chamber is washed thoroughly with saline. The pupil is contracted with intraocular acetylcholine 1%, carbachol 0.01%, or pilocarpine 0.5% solution. The incision is closed by hydrating the corneal incisions. A suture rarely is needed.

In another embodiment, for implantation of the intraocular lens assembly of the invention, the main incision is made at the ventral area of the eye (at the "top" of the eye, at "12 o'clock"). The width is preferably equal to the size of the optic, which may be 4–5 mm. Side incisions are made, approximately 1 mm wide. The lens assembly of the invention is inserted then vertically. The lens assembly of the invention is rotated inside the viscoelastic-filled anterior chamber; the haptics are placed horizontally.

Fixating the lens assembly of the invention is a bimanual procedure. Lens assemblies are implanted using special tools to compress the haptics, such as forceps or cannulae, or rely on microhooks to manipulate the optic through a hole in the surface of the optic (see discussion in U.S. Pat. No. 6,142,999). A vertically-holding lens forceps, which enters the anterior chamber through the main incision, centers the optic on the pupil and holds it steadily. A thin forceps is introduced from the side incision and grasps the iris close to the claw, passing a fold of the iris through the claw, and results in fixing one of the haptics. Both instruments are withdrawn, and the surgeon changes hands for holding each tool. The anterior chamber of the eye is again deepened with viscoelastic material, and the lens-fixation instruments are reintroduced. The second haptic-fixation maneuver is performed through the incision on the opposite side.

A peripheral iridectomy is can then be performed. Then, the introduced viscoelastic material (if any) is aspirated through the three incisions. The anterior chamber is gently irrigated and inflated with air to remove all viscoelastic material.

For closure of the incision line, the apposition of the sides of the incision may be achieved by one or two superficial sutures. Alternatively, a large air bubble may be left inside the anterior chamber to effect an apposition. If the limbal incision was made without a pocket, then a closure of the incision line should be performed using sutures.

At the end of the surgery, 20 mg of gentamycin and 2 mg of dexamethasone are subconjunctivally injected. A sterile pad and a protective shield are applied.

Alternatively, the intraocular lens assembly of the invention can be located in the posterior chamber of the eye, using methods known to those of skill in the ophthalmic art (see, U.S. Pat. No. 6,110,202; Pesando et al., 15(4) J. Refract Surg. 415–23 (1999); Sanders et al., 15(3) J. Refract Surg309–15 (1999). In posterior chamber implants, the haptics normally lodge in the ciliary sulcus.

Aphakic intraocular lens assembly implantation is also usefully provided for by the intraocular lens assembly of the invention. The lens assembly can be surgically implanted in the evacuated capsular bag of the lens of an eye (for example, through the anterior capsule opening in the bag) in a position such that the lens optic of the intraocular lens assembly is aligned with the opening defined by the anterior capsular remnant, and the outer ends of the lens distal portions are disposed within the outer perimeter of the bag. The intraocular lens assembly of the invention has a radial dimension from the outer end of each distal or extended portion to the axis of the intraocular lens assembly. Thus, with the intraocular lens assembly implanted within the capsular bag, the outer ends of the extended portions engage the inner perimetrical wall of the capsular bag with no or minimal stretching of the bag. After implantation of the intraocular lens assembly in the capsular bag, active ectodermal cells on the posterior surface of the anterior capsule rim of the bag cause fusion of the rim to the elastic posterior capsule of the bag by fibrosis about the lens extended portions. Because of the haptic design, the intraocular lens assembly of the invention can, when placed in the capsular bag of the eye, provide accommodation for the patient.

Advantageously, post-operative atropinization of the optic ciliary muscle is not required for the intraocular lens assembly of the invention (when implanted either as a refractive phakic intraocular lens or an aphakic intraocular lens) to achieve accommodation. During surgery, especially for implantation of aphakic intraocular lenses, the ciliary muscle of the eye had previously and typically been paralyzed with a ciliary muscle relaxant to place the muscle in its relaxed state. Ciliary muscle relaxants include anticholinergics such as atropine, scopolamine, homatropine, cyclopentolate and tropicarnide. Atropine is preferred. Proprietary preparations of atropine include Isopto Atropine (eye drops); Minims Atropine Sulphate (single-dose eye drops); Min-I-Jet Atropine (injection); Actonorm Powder (combined with antacids and peppermint oil); Atropine-1; Atropine-Care; Atropisol; Isopto Atropine; Ocu-tropine; Atropair; Atropine Sulfate S.O.P.; Atrosulf; I-Tropine; Isopto Atropine; and Ocu-Tropine. Prior to this invention (i.e., while implanting intraocular lenses not having the advantages of the foldable intraocular lens assembly of the invention), the patient's eye would be atropinized following surgery, to allow for accommodation of the lens of the implanted aphakic intraocular lens assembly to the eye (see discussion, U.S. Pat. No. 6,051,024). Following surgery, the ciliary muscle relaxant (such as atropine) would be periodically introduced throughout a post-operative fibrosis and healing period (such as two to three weeks) to maintain the ciliary muscle in its relaxed state until fibrosis was complete. This drug-induced relaxation of the ciliary muscle prevented contraction of the ciliary muscle and immobilized the capsular bag. Thus, the implanted intraocular lens optic fixed during fibrosis in its distant vision position within the eye relative to the retina (accommodation). The implanted lens pressed backward against and thereby forwardly stretched the elastic posterior capsule of the capsular bag. By contrast, because of the haptic design of the intraocular lens assembly of the invention, the lens can, when placed in the capsular bag of the eye, provide accommodation for the patient without the administration of post-operative atropine.

It will be apparent to those skilled in the art that other changes and modifications can be made in the above-described invention and methods for making and using the same, without departing from the scope of the invention herein, and it is intended that all matter contained in the above description shall be interpreted in an illustrative and not in a limiting sense.

I claim:

1. An intraocular lens assembly, comprising:
   a lens having a circumferential edge, and a first haptic and a second haptic, said first and second haptics extending from said lens, wherein each of said haptics include:
   (a) a first leg extending from said edge to a distal end thereof;
   (b) a second leg extending from said edge to a distal end thereof;
   (c) a transverse member extending between said distal ends of said first and second legs, said transverse member being substantially straight or bowed inward toward said lens; and
   (d) a footplate at each of said distal ends.

2. The intraocular lens assembly of claim 1, wherein the first leg is selected from the shapes consisting of inwardly bowing, straight, and outwardly bowing.

3. The intraocular lens assembly of claim 1, wherein said second leg is selected from the shapes consisting of inwardly bowing, straight, and outwardly bowing.

4. The intraocular lens assembly of claim 1, wherein said first and said second legs of said first and second haptic are the same shape.

5. The intraocular lens assembly of claim 1, wherein said first and second legs of said first and second haptics are differently shaped.

6. The intraocular lens assembly of claim 1, wherein each of said first and second legs of each of said first and second haptics is outwardly bowing.

7. The intraocular lens assembly of claim 1, wherein each of said first and second legs of each of said first and second haptics is inwardly bowing.

8. The intraocular lens assembly of claim 1, wherein the lens assembly is made from a flexible material.

9. The intraocular lens assembly of claim 8, made of a material selected from the group consisting of hydrogel, collagen, collamar, collagel, acrylate polymers, methacrylate polymers, silicone polymers, and composites thereof.

10. The intraocular lens assembly of claim 9, wherein said lens assembly is foldable.

11. The intraocular lens assembly of claim 9, wherein said lens assembly is firm.

12. A method for implanting a phakic intraocular lens assembly in an eye, comprising:
   inserting into the eye a lens having a circumferential edge, and a first haptic and a second haptic, said first and second haptics extending from said lens, wherein each of said haptics include:
   (a) a first leg extending from said edge to a distal end thereof;
   (b) a second leg extending from said edge to a distal end thereof;
   (c) a transverse member extending between said distal ends of said first and second legs, said transverse member being substantially straight or bowed inward toward said lens; and
   (d) a footplate at each of said distal ends.

13. The method of claim 12, wherein intraocular assembly is inserted in the anterior chamber of the eye.

14. The method of claim 13, wherein intraocular assembly is inserted anterior the iris.

15. The method of claim 13, wherein intraocular assembly is inserted posterior to the iris.

16. The method of claim 12, wherein intraocular assembly is inserted in the posterior chamber of the eye.

17. A method for implanting an aphakic intraocular lens assembly in an eye, the eye having a natural capsular bag attached about its perimeter to the ciliary muscle of the eye and from which the natural lens matrix has been removed, comprising:
   (1) inserting into the capsular bag of the eye a lens having a circumferential edge, and a first haptic and a second haptic, said first and second haptics extending from said lens, wherein each of said haptics include:
   (a) a first leg extending from said edge to a distal end thereof;

(b) a second leg extending from said edge to a distal end thereof;
(c) a transverse member extending between said distal ends of said first and second legs, said transverse member being substantially straight or bowed inward toward said lens; and
(d) a footplate at each of said distal ends;
(2) permitting the eye to heal in the absence of a ciliary muscle relaxant; wherein the implanted intraocular lens provides an accommodating lens to the eye.

* * * * *